United States Patent [19]
Springer, Jr. et al.

[11] Patent Number: 4,984,571
[45] Date of Patent: Jan. 15, 1991

[54] COLLAPSIBLE TANNING BOOTH

[75] Inventors: Jack F. Springer, Jr., Fort Edward; Timothy S. Smith, Queensbury; Cathy A. Cloutier, Glens Falls; Ben A. Marcantonio, South Glens Falls; Richard A. Willis, Hudson Falls, all of N.Y.

[73] Assignee: KVR Manufacturing Corp., Hudson Falls, N.Y.

[21] Appl. No.: 370,337

[22] Filed: Jun. 22, 1989

[51] Int. Cl.$^5$ .............................................. A61N 5/06
[52] U.S. Cl. ..................................... 128/371; 128/396
[58] Field of Search ............... 128/372, 376, 395, 396, 128/371, 377; 250/504 R; 362/218

[56] References Cited

U.S. PATENT DOCUMENTS

| | | | |
|---|---|---|---|
| D. 248,968 | 8/1978 | McMillan | 128/396 |
| 828,733 | 1/1906 | Fuller | 128/371 |
| 4,100,415 | 7/1978 | Blaisdell | 128/371 |
| 4,287,554 | 9/1981 | Wolff | 362/218 |
| 4,335,724 | 6/1982 | Frei et al. | 128/395 |
| 4,444,189 | 4/1984 | Seiverd | 128/395 |
| 4,469,102 | 9/1984 | Fish | 128/395 |
| 4,660,561 | 4/1987 | Nielsen | 128/376 |
| 4,674,507 | 6/1987 | Basso | 128/396 |
| 4,683,886 | 8/1987 | Kramer et al. | 128/376 |

FOREIGN PATENT DOCUMENTS

| | | | |
|---|---|---|---|
| 3023752 | 1/1982 | Fed. Rep. of Germany | 128/396 |
| 3630060 | 3/1988 | Fed. Rep. of Germany | 128/396 |
| 522055 | 3/1955 | Italy | 128/371 |
| 10338 | of 1901 | United Kingdom | 128/371 |

OTHER PUBLICATIONS

Advertisement of Tanning Hut Systems, Inc., 4/1988.
Brochure of Klafsun WolffSystem SW-36.
Brochure of Tan America Systems.
Brochure of The Klafsun Favorit 16L.
Brochure of The Klaufson Klafsunny II.
Brochure of SCA Wolff System 124SL or 224SL.
Brochure of The Alisun C-Series.
Brochure of Sun Industries.

Primary Examiner—Edward M. Coven
Assistant Examiner—M. Graham
Attorney, Agent, or Firm—Brumbaugh, Graves, Donohue & Raymond

[57] ABSTRACT

A collapsible tanning booth comprises at least two rear lamp units and at least two front lamp units, each of the units having a thin long casing that includes rear, side, top and bottom walls and a front panel, the front panel being of a material transmissive to ultraviolet light, a reflector panel adjacent the rear wall and lamps mounted between the reflector panel and the front panel. The rear lamp units are hinged together along their adjacent side walls so that they can be moved between a storage configuration in which they are substantially aligned transversely and a use configuration in which they are oblique transversely to each other. The laterally outermost front units are hinged along their laterally outermost side walls to the laterally outermost side walls of the rear lamp units so that the front units can be moved between a storage configuration in which they reside face to face against the rear lamp units and a use configuration in which they are disposed oblique to the rear lamp units and to each other. Two adjacent front lamp units, however, are unattached to each other to enable pivotal movement of such units about their hinges apart from each other to provide an opening for access by a person to a space defined by the units in their use configuration.

4 Claims, 2 Drawing Sheets

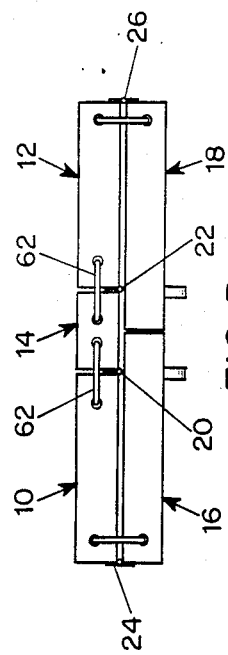
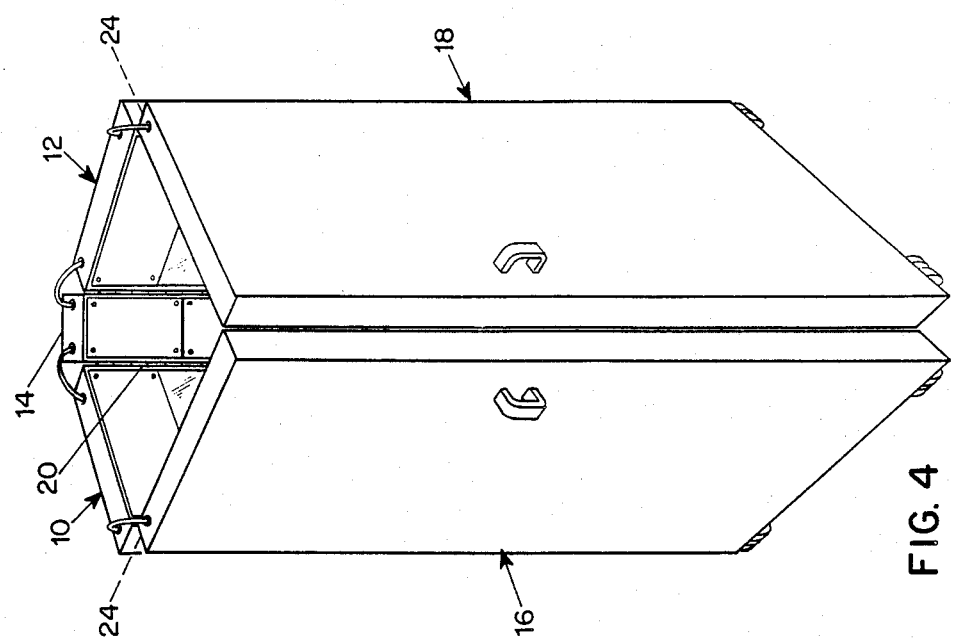
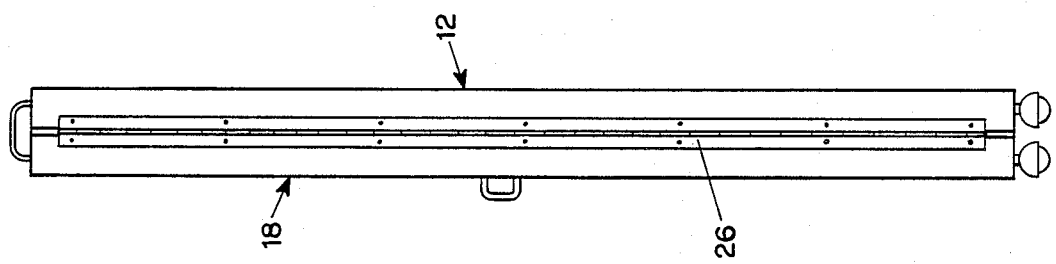
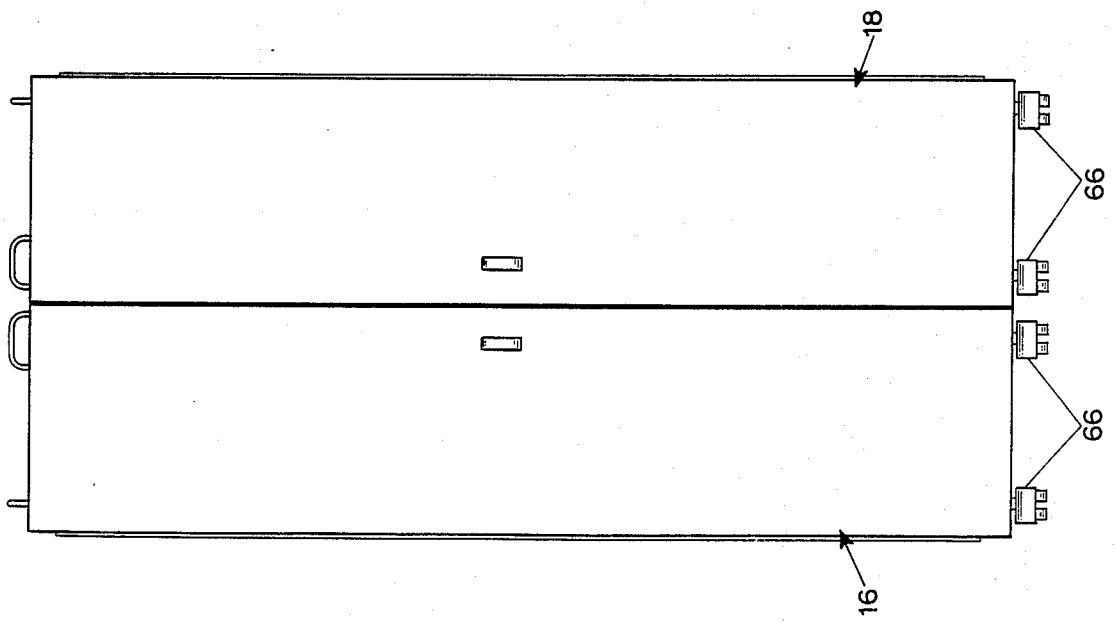

COLLAPSIBLE TANNING BOOTH

DESCRIPTION

1. Field of the Invention

The present invention relates to ultraviolet light tanning apparatus of the type in which the entire body of the user is simultaneously and substantially uniformly illuminated by ultraviolet alpha rays (U.V.A.) to produce skin tanning.

2. Background of the Invention

There are three basic types of U.V.A. tanning apparatus being marketed commercially. One type is a tanning bed that consists of elongated, horizontally disposed lower and upper lamp units—the user lies on the lower unit, and the upper unit is positioned above him or her. Kramer U.S. Pat. No. 4,683,886 (1987) elaborate, tanning bed. In this regard the available tanning beds cost in the range of $3,000 to $6,000. They also require about 20 square feet or more of floor space. The cost and the space requirement makes them impractical for any setting other than commercial health and recreation centers and exercise rooms in more elaborate homes. Many people feel that tanning beds resemble coffins, and such people may be not only a bit uncomfortable physically lying on the hard surface of the lower lamp unit but also psychologically ill at ease encased in a coffin-like device.

A second type of tanning apparatus is the vertical tanning booth. Tanning booths are polygonal or oval in design, about seven feet tall, and some 40 inches across, and are not unlike telephone booths or shower stalls. There is access through a door. Like tanning beds, the tanning booths on the market are expensive (price range $4,000 to $7,000) and take up a lot of space. Fish U.S. Pat. No. 4,469,102 (1984) describes and shows a fairly typical tanning booth.

The third type is a tanning canopy, which is a single elongated, flat or curved panel unit about three feet wide and seven feet long and mounted on a stand that allows it to be set up horizontally above a bed or lounge or vertically so the user can stand in front of it. Tanning canopies are the least expensive type of tanning apparatus, (price range $900 to $2,000) occupy the least amount of space, and can be rolled away on their caster-equipped stand for storage after use. They are, therefore, practical for residential use and have been the most successful of the three types in the residential market. They have the disadvantage, however, of doing only one side of the body at a time, so full-body tanning requires a session time twice as long as that required in a bed or booth.

There has been at least one proposal in the somewhat related field of phototherapy for medical treatment of skin disorders for a portable U.V. phototherapy device. Seiverd U.S. Pat. No. 4,444,189 (1984) describes and shows a treatment booth composed of two collapsible carrying cases. Each case has lamps on the insides of a rear panel and a hinged front panel. Half of the lamps are on panels that slide lengthwise of the main panels of the cases to increase the height of the apparatus. Setting the apparatus up and taking it down appears to be a complicated process. Also, the lamps are not protected when the apparatus is set up for use, and while the apparatus is designed to be transported, carrying handles being provided for that purpose, each case would probably weigh more than many people can handle comfortably.

SUMMARY OF THE INVENTION

One object of the present invention is to provide a collapsible tanning apparatus that does the entire body and that can be stored unobtrusively. Another object is to provide a tanning apparatus that is easy to set up for use and to collapse for storage. Still another object is to provide a collapsible tanning booth that is of relatively simple construction and that can be produced and sold economically. The tanning apparatus of the present invention is, accordingly, ideally suited to the home or office market.

The foregoing another objects are met, according to the present invention, by a collapsible tanning booth comprising at least two rear lamp units and at least two front lamp units. Each of the units has a thin elongated casing that includes rear, side, top and bottom walls and a front panel, the front panel being of a material transmissive to ultraviolet light. A reflector panel is mounted adjacent the rear wall of the casing and lamps are mounted in the casing between the reflector panel and the front panel. The rear lamp units are hinged together along their adjacent side walls so that they can be moved between a storage configuration in which they are substantially aligned transversely and a use configuration in which they are oblique to each other transversely. The laterally outermost front units are hinged along their laterally outermost side walls to the laterally outermost side walls of the rear lamp units so that the front units can be moved between a storage configuration in which they reside face to face against the rear lamp units and a use configuration in which they are disposed oblique to the rear lamp units and to each other. Two adjacent front lamp units are, however, unattached to each other to enable pivotal movement of such units about their hinges apart from each other to provide an opening for access by a person to a space defined by the units in their use configuration.

In a preferred embodiment, there is a columnar enclosure in the form of a narrow elongated closed box that is vertically oriented and located between and hinged to two adjacent rear lamp units. Each lamp unit includes a compartment in the uppermost part of the case containing ballasts for the lamps. Casters on the bottom panels of the casings of all of the lamp units enable the units to be readily moved between their storage and use configurations. The adjacent side walls of the front lamp units that are not hinged to each other meet when all of the lamp units are in the storage configuration.

For a better understanding of the invention, reference can be made to the following description of an exemplary embodiment, taken in conjunction with the accompanying drawings.

DESCRIPTION OF THE DRAWING

FIGS. 1 to 3 are front, side and top elevational views, respectively, of the embodiment in its collapsed configuration.

FIG. 4 is a pictorial view of the front of the embodiment in its use configuration.

DESCRIPTION OF THE EMBODIMENT

Figure 5:
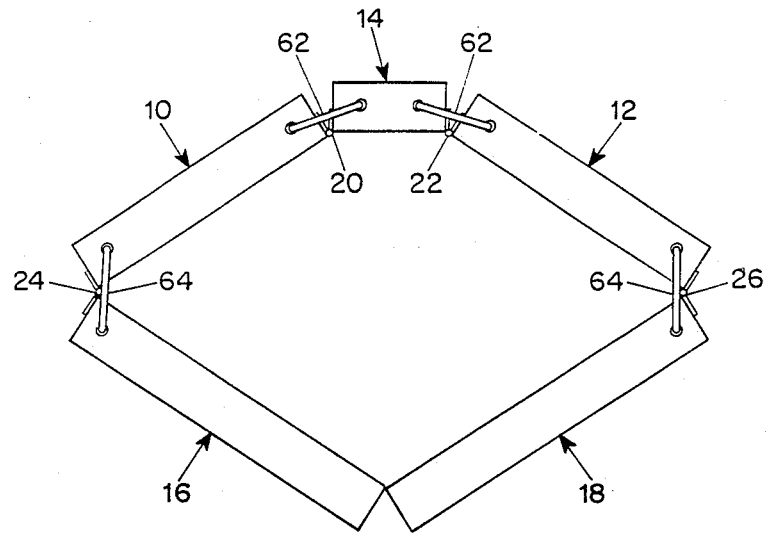
FIG. 5 is a top view of the embodiment in its use configuration.

The embodiment comprises two rear lamp units 10 and 12, a narrow closed box 14, and two front lamp units 16 and 18. The rear lamp units 10 and 12 straddle the box 14 and are joined to it by hinges 20 and 22. Each front lamp unit 16, 18 is joined to a rear lamp unit 10, 12 by a hinge 24, 26 at the laterally outer side of the respective rear units.

The lamp units 10, 12, 16, 18 are of substantially identical construction, the main difference being that the front units are wider than the rear units by an amount equal to one-half the width of the box 14. Each lamp unit has a thin, vertically elongated rectangular casing that consists of a unitary box-like structural body 30 which has a rear wall 32, side walls 34, 36, a top wall 38 and a bottom wall 40 and is, preferably, fabricated from 20 gauge steel sheet stock. An inturned flange 42 along the front edge of the side, top and bottom walls provides a land area and attachment point for the front panels of the casing. The primary front panel of each lamp unit casing is a rectangular sheet 44 of "Plexiglas ®" or of some other material that transmits U.V.A. light. At the top of each casing 30 is a ballast panel 46 fabricated from steel sheet and having a shelf portion 48 on which the lamp ballast (not shown) is mounted. A lamp holder 50 fabricated from sheet steel is installed in the top portion of the casing 30 and has a mounting flange portion 52 for conventional lamp sockets (not shown). Also not shown is a lamp holder mounted on the bottom wall for the bottom lamp sockets.

Figure 6:
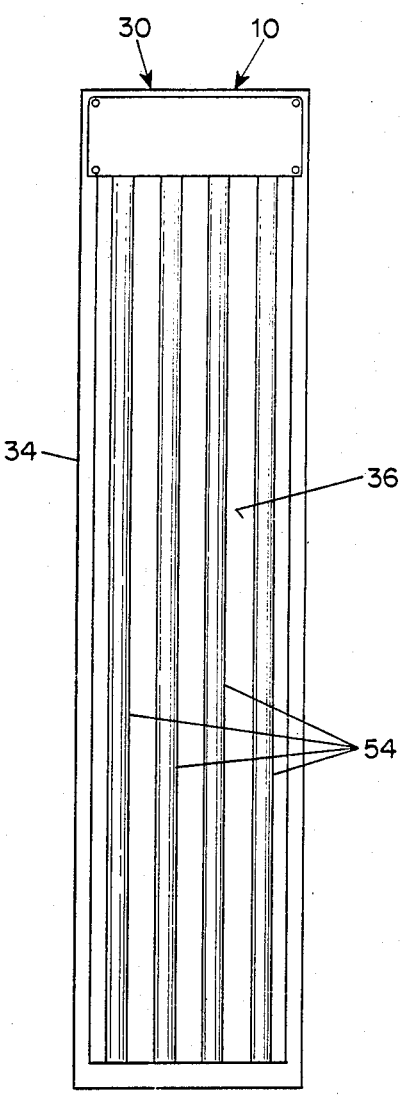
FIG. 6 is a front elevational view of one of the lamp units.
Figure 8:
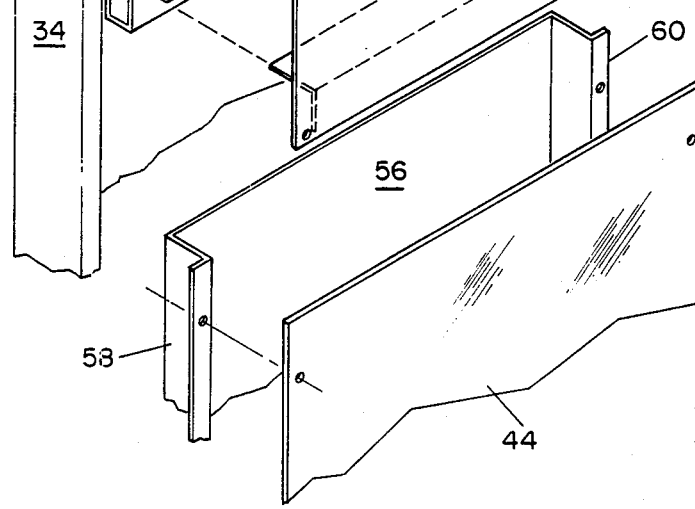
FIG. 8 is an exploded pictorial view of the top portion of a lamp unit.
Figure 7:
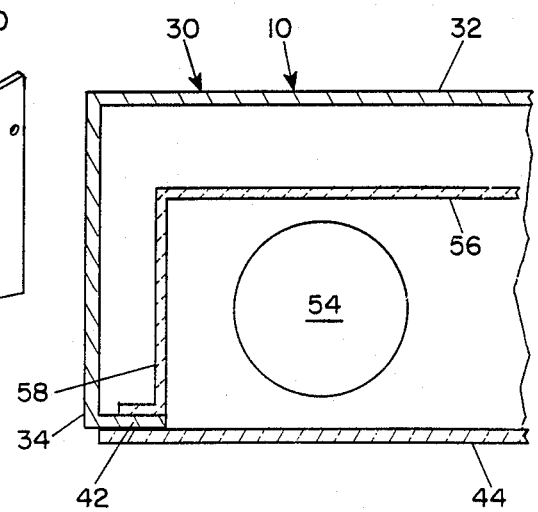
FIG. 7 is a partial transverse cross-sectional view of a lamp unit.

Each lamp unit has four U.V.A. lamps 54 (FIG. 6) and a reflector, such as a panel 56 of polished aluminum mounted behind the lamps by means of side flanges 58, 60.

The box 14 is constructed in much the same way as the casings of the lamp units in that it is simply an open rectangular body having one or more removable front panels. The box 14 serves as a cable conduit for the power cord, which enters at or near the bottom and runs up to a switch in the front panel. The lamp units are wired to the switch by wires that leave the top of the box and pass through flexible sheaths 62 to the respective rear units 10 and 12. Similarly, wires lead from unit 10 to unit 16 and from unit 12 to unit 18 through sheaths 64 at the top.

Many of the details of the embodiment (e.g., sockets, wiring, switches, and fasteners) are not shown or described because they are well within the ability of one of ordinary skill in the art to design. Also not shown are vent holes in the bottom and top walls of each lamp unit casing to promote convective cooling of the unit.

Each of the two rear lamp units has two double-wheeled carpet casters 66 attached to the bottom panel, one adjacent each end, and each front lamp unit also has a caster 66 attached near the free end (the end remote from the hinge). The casters make it easy to move the booth from place to place and to change it back and forth between the storage configuration (FIGS. 1 to 3) and the use configuration. In particular, by pushing the front units 16 and 18 toward the rear units 10 and 12, the former are brought face to face with the latter and the latter are brought into lateral alignment (FIG. 3) by pivoting of the units at the hinge connections. The booth is made ready for use by pulling out the front units 16 and 18 and positioning them and the rear units 10 and 12 in the configuration shown in FIG. 5 in which the adjacent units are oblique to each other and define a compartment.

The advantages provided by the invention of ease of use, small footprint for storage, simple construction and full-body tanning are readily apparent. The back walls of the front lamp units can be given a decorative treatment—e.g., panel doors resembling cabinetry—that is compatible with residential and office spaces of various designs. The box of the apparatus can be fastened to a wall for a built-in installation. Other cabinetry can be placed side by side with the apparatus. As for the footprint, a suitable overall size for the apparatus in its collapsed configuration is 6"×36"×78", which means a 1.5 sq. ft. footprint.

Ideally, the apparatus has four lamp units, as in the illustrated embodiment, but up to eight units is possible and will give a little more uniform illumination than four units. At a small sacrifice in collapsed size, the lamp units can be moderately curved transversely.

We claim:

1. A collapsible tanning booth comprising at least two rear lamp units and at least two front lamp units, each of the lamp units having a thin long casing that includes rear, side, top and bottom walls and a front panel, the front panel being of a material transmissive to ultraviolet light, a reflector panel adjacent the rear wall and lamps mounted between the reflector panel and the front panel, the rear lamp units being arranged side by side and the front units being arranged side by side, first hinge means joining the rear lamp units together along adjacent side walls of the casing thereof for articulation relative to each other between a storage configuration in which they are substantially aligned transversely and a use configuration in which they are oblique transversely to each other, second hinge means joining each laterally outermost front unit along a laterally outermost side wall thereof to a laterally outermost side wall of a corresponding laterally outermost rear lamp unit so that the front units can be moved between a storage configuration in which they reside face to face against the rear lamp units and a use configuration in which they are disposed oblique to the rear lamp units and to each other, two adjacent front lamp units, however, being unattached to each other to enable pivotal movement of such units about the second hinge means apart from each other to provide an opening for access by a person to a space defined by the units in their use configuration, and roller support means on the bottom walls of the casings of all of the units for supporting the units on a floor for rolling movements thereof between the storage configuration and use configuration.

2. A collapsible tanning booth according to claim 1 and further comprising a narrow elongated closed box that is disposed vertically and located between two laterally mutually adjacent rear lamp units, and wherein the first hinge means joins said adjacent rear lamp units to said box.

3. A collapsible tanning booth according to claim 1 wherein each lamp unit includes a compartment in the uppermost part of its casing containing ballasts for the lamps.

4. A collapsible tanning booth according to claim 1 wherein adjacent side walls of said front lamp units meet when all of the lamp units are in the storage configuration.

* * * * *

UNITED STATES PATENT AND TRADEMARK OFFICE
CERTIFICATE OF CORRECTION

PATENT NO. : 4,984,571

DATED : January 15, 1991

INVENTOR(S) : Jack F. Springer, Jr. et al.

It is certified that error appears in the above-identified patent and that said Letters Patent is hereby corrected as shown below:

First page, 2nd col., line 3, "Klaufson" should read --Klafsun--;
Col. 1, line 18, after "(1987)" insert --describes and shows a typical, albeit very costly and--;
Col. 4, line 33, "casing" should read --casings--.

Signed and Sealed this

First Day of December, 1992

Attest:

DOUGLAS B. COMER

Attesting Officer

Acting Commissioner of Patents and Trademarks